(12) United States Patent
Crosby (10) Patent No.: US 8,534,292 B1
(45) Date of Patent: Sep. 17, 2013

(54) PERSONAL TUNER

(75) Inventor: Charles Crosby, Orlando, FL (US)

(73) Assignee: CAMS Medical Instruments, Inc., Orlando, FL (US)

(*) Notice: Subject to any disclaimer, the term of this patent is extended or adjusted under 35 U.S.C. 154(b) by 283 days.

(21) Appl. No.: 12/910,525

(22) Filed: Oct. 22, 2010

Related U.S. Application Data (60) Division of application No. 11/441,483, filed on May 26, 2006, now Pat. No. 7,883,534, which is a continuation-in-part of application No. 10/084,008, filed on Feb. 27, 2002, now Pat. No. 7,077,857.

(60) Provisional application No. 60/685,448, filed on May 27, 2005.

(51) Int. Cl.
*A61B 19/00* (2006.01)
*A61N 5/06* (2006.01)

(52) U.S. Cl.
USPC .............................................. 128/898; 607/88

(58) Field of Classification Search
USPC ..................... 606/88–91, 93, 96–101; 606/3, 606/10, 13; 604/20, 21; 128/898
See application file for complete search history.

(56) References Cited

U.S. PATENT DOCUMENTS

| | | |
|---|---|---|
| 1,510,080 A | 9/1924 | Murphy |
| 2,306,909 A | 12/1942 | Sykes |
| 2,312,670 A | 3/1943 | Olds |
| 3,371,234 A | 2/1968 | Cady |
| 4,708,127 A | 11/1987 | Abdelghani |
| 4,739,507 A | 4/1988 | Byer |
| 4,869,666 A | 9/1989 | Talass |
| 5,158,070 A | 10/1992 | Dory |
| 5,230,334 A | 7/1993 | Klopotek |
| 5,464,436 A | 11/1995 | Smith |
| 5,989,202 A | 11/1999 | Noda |
| 6,113,559 A | 9/2000 | Klopotek |
| 6,217,530 B1 | 4/2001 | Martin |
| 6,238,421 B1 | 5/2001 | Gunther |
| 6,500,198 B1* | 12/2002 | Southard .......................... 607/88 |
| 6,722,772 B2 | 4/2004 | Maglica |
| 6,813,289 B2 | 11/2004 | Gruzdev |
| 2004/0130896 A1* | 7/2004 | Brown et al. .................. 362/259 |

OTHER PUBLICATIONS

Mini Maglite Flashlight Specifications, http://web.archive.org/web/20030814145336/www.maglite.com/product_anatomy.asp? psc=2AACELL.

(Continued)

*Primary Examiner* — Ahmed Farah
(74) *Attorney, Agent, or Firm* — Brian S. Steinberger; Law Offices of Brian S. Steinberger, P.A.

(57) ABSTRACT

Handheld flashlight type vibratory therapeutic treatment invention, devices, and methods that can house a small piezoelectric crystal adjacent to a bulb in the emitting chamber portion of a flashlight housing, where the crystal is located next to or between light source, or off-axis to the light emitting beam of the flashlight. The crystal can generate a fixed output of approximately 7 to approximately 8 Hertz while the flashlight body is positioned up to approximately 18 inches over the body part being treated with a light beam from the bulb being aimed at the area to be treated. Treatment effectiveness can occur within approximately 2 minutes of being treated. The flashlight invention can be used for treating a variety of ailments such as inflammations, nerve problems, joint pain, muscle pain, as well as gall bladder type problems.

18 Claims, 6 Drawing Sheets

(56) References Cited

OTHER PUBLICATIONS

Liss Body Stimulator, Professional Instrument Manual, SBL 502-B, 1994, pp. 1-8.
Tenscam Professional Manual, Charles Crosby, 2001, pp. 1-8.
Oschman, Energy Medicine, The Scientific Basis, Churchill Livingstone Publishers, 2000, pp. 51, 61, 184.

* cited by examiner

PERSONAL TUNER

This is a Divisional of U.S. patent application Ser. No. 11/441,483 filed May 26, 2006, now U.S. Pat. No. 7,883,534, which is a Continuation-In-Part of U.S. patent application Ser. No. 10/084,008 filed Feb. 27, 2002, now U.S. Pat. No. 7,077,857, and this invention claims the benefit of priority to U.S. provisional patent application Ser. No. 60/685,448 filed May 27, 2005, all of which are incorporated by reference.

FIELD OF INVENTION

This invention relates to medical therapy treatment devices, and in particular to devices, apparatus and methods of using a portable single handheld tool that generates vibratory emissions, ultrasonic emissions, light pulses and/or electromagnetic emissions which focus the energy emissions to patients for therapeutic treatments.

BACKGROUND AND PRIOR ART

Ultrasound and vibratory type emitting devices have been used for medical therapeutic applications over the years. Various types of therapeutic devices have been proposed that apply ultrasonic oscillations and vibrations directly to an affected body part so as to relax muscles, quicken blood flow circulation, enhance healing of the skin, etc. See For example, U.S. Pat. Nos. 4,708,127 to Abdelghami; 5,230,334 and 6,113,559 to Klopotek; and 5,989,202 to Noda et al.

However, these devices and systems have practical type limitations. For example, most of these devices are limited to direct contact of a portion of the device itself against the skin of the patient. As a result, the field of application is generally restricted to the areas directly beneath the skin contact point. The body contacting requirement does not allow these devices to easy slide over and across one's skin to different areas to be treated. Thus, moving these devices to other body areas usually requires that the device be physically raised, moved and lowered again to the area to be treated.

Furthermore, these devices are generally limited to using acoustical type vibratory signal emissions from a single generator type unit such as an electromagnetic generator, and does not use other energy sources, nor applies other energy emissions for treatments. Still furthermore, the single generators are generally limited to generating only fixed frequency outputs.

The subject inventor has previously sold a basic handheld tool entitled: Tens Cam having a single fixed frequency generating crystal that solely relied on an electromagnetic induction coil to drive a single crystal. The Tens Cam unit consisted only of a Coil wrapped around a longitudinal Crystal, powered by LISS BODY STIMULATOR power pack, where LEDs (light emitting diodes) are used to indicate power being turned on.

The operation of the Tens Cam used a fixed frequency of approximately 8 Hertz that was generated by an electromagnetic source in a narrow beam having a diameter of approximately 1 to approximately 2 millimeters. The delay time for therapeutic effects of the Tens Cam unit was between approximately two to approximately four (4) minutes.

The Tens Cam unit had problems due to it's' weight of approximately one pound and its' rough appearance and oblong shape. Taking up to four minutes to generate therapeutic effects on the patient was difficult to do over continuous treatments, since it required the operator to physically hold the one pound unit in a raised position above the patient being treated. Thus, operator fatigue was an inherent result of using this unit.

By physically holding the vibrating unit above a patient throughout a several minute treatment process the operator received direct vibratory effects from the unit. The combination of constantly holding the weight of the unit and the direct vibratory effects, along with the operator being constantly within the generation field of the unit created side effects such as but not limited to fatigue and malaise for the operator. Operators repeatedly using the Tens Cam have complained of side effects of medium nerve paraethias, which is a numbness and tingling effect to their hands and fingers.

Additional problems with the Tens Cam unit as with other electromagnetic and with vibratory units is that all these units can be known to give off heat which has caused tissue damage. Furthermore, theses prior art type units have limitations as to the tissue penetration being achieved, since the tissue penetration depth is limited by the mechanical nature of the vibrations.

All of the prior art units are limited to generating energy directly from electric power supplies and fail to take in additional energy to aid in the therapy treatment. Ambient energy is not used by the prior art devices.

Prior art units have been known to cause injuries directly to the patients. Using a strictly handheld supported vibrating and/or heat generating and/or electrically driven device can potentially injure the patients themselves, if the operator directly contacts the patients with the devices. Electric shocks, burns and other damage can be caused by the patients coming into direct contact with many prior art therapy devices.

Thus, the need exists for solutions to the problems with the prior art devices.

SUMMARY OF THE INVENTION

A primary objective of the invention is to provide a handheld tool, apparatus, device and method for therapy treatments that does not have to be in direct contact with the skin surface of a patient, that does not have the tissue depth penetration limitations of electromagnetic sources and vibratory devices.

A secondary objective of the invention is to provide a handheld tool, apparatus, device and method for therapy treatments that can combine an energy generating source along with an ambient receiver to effect medical treatment effects at resonating emissions of approximately 7 to approximately 8 Hertz.

A third objective of the invention to provide a handheld tool, apparatus, device and method for therapy treatments that can alternate between a fixed frequency output and a variable frequency range of emissions to include the resonant frequency of the patient being treated of between approximately 4 to approximately 15 Hertz.

A fourth objective of the invention is to provide a handheld tool, apparatus, device and method for therapy treatments that can be positioned toward a body part to be treated.

A fifth objective of the invention is to provide a handheld tool, apparatus, device and method for therapy treatments that reduces and eliminates patient injury risks, and allows for most any body tissue to be easily reached and treated by the tool.

A sixth objective of the invention is to provide a handheld tool, apparatus, device and method for therapy treatments that reduces and potentially eliminates fatigue and malaise injuries to the tool operator or previously known devices.

A seventh objective of the invention is to provide a handheld tool, apparatus, device and method for therapy treatments that can achieve therapeutic results within approximately 2(two) minutes as compared up to 4 (four) minutes that was required with previous tools.

Various embodiments for using the invention are disclosed. One embodiment can use a flash lamp generator that generates with side crystals and a main crystal with lens, a variable 4 to approximately 15 Hertz output in a approximately 5 to approximately 6 diameter beam positioned up to approximately 18 inches over the body part being treated. Treatment effectiveness has occurred within approximately 2 minutes of being treated.

Another embodiment can use an electromagnetic generator with the main crystal and side crystals and output lens to generate a fixed output of approximately 7 to approximately 8 Hertz. A still another embodiment combines the previous embodiments.

A small portable flashlight sized version embodiment can also be used. This embodiment can house a small crystal adjacent to a bulb in the emitting chamber portion of a flashlight housing, where the crystal is located between or off-axis to the light emitting beam of the flashlight. The crystal can generate a fixed output of approximately 7 to approximately 8 Hertz while the flashlight body is positioned up to approximately 18 inches over the body part being treated. Treatment effectiveness can occur within approximately 2 minutes of being treated. A flashing version of the flashlight has shown to be effective treatment with a pulsed signal of approximately 8 Hz being generated.

The novel tools can be powered by a wall plug, batteries, combinations thereof, and the like. The flashlight version can be powered by a windup handle that allows a battery to be continuously charged within the handheld unit.

Further objects and advantages of this invention will be apparent from the following detailed description of a presently preferred embodiment which is illustrated schematically in the accompanying drawings.

DESCRIPTION OF THE PREFERRED EMBODIMENTS

Before explaining the disclosed embodiments of the present invention in detail it is to be understood that the invention is not limited in its application to the details of the particular arrangements shown since the invention is capable of other embodiments. Also, the terminology used herein is for the purpose of description and not of limitation.

Figure 1:
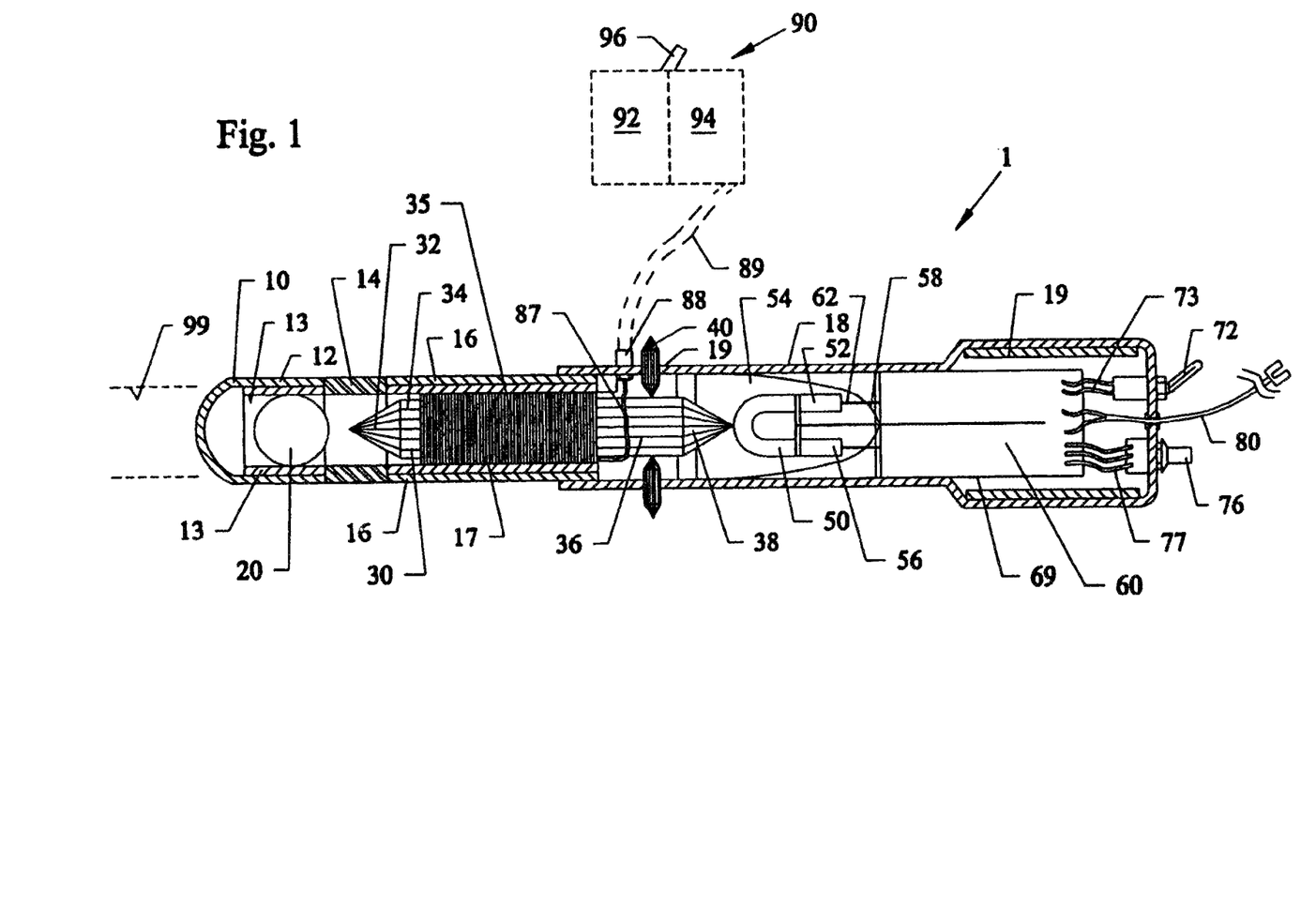
FIG. 1 is a cross-sectional view of a novel pulse cam device invention.

FIG. 1 is a cross-sectional view of a novel pulse cam device invention 1. The device 1 can include a lens emitting end cap 10 and sleeve 12 which can be formed from a flexible transparent plastic, and the like. Within sleeve 12, can be a secondary cylindrical sleeve also formed from a plastic transparent material that can be used to support a divergent lens 20 as a combined diffuser and amplifier, such as but limited to a crystal sphere formed from silicon dioxide, quartz, and the like. In the preferred embodiment, the sphere used as lens 20 can have a diameter of approximately 4.5 cm.

The base of the cap and sleeve 12 can abut against a cylindrical plastic type clear sleeve window that allows one to view the flashing of the strobing crystal 30 which will be described in detail later. A middle cylindrical sleeve 16 is joined to the window sleeve 12, and a rear cylindrical sleeve housing 18 such as a PVC pipe, attaches to the middle cylindrical sleeve 16, which expands to a closed cap end 19.

A press joint 13 within sleeve 12 allows for a tight machine fit between components to fixably support the lens 20. A second press joint 17 can be located within middle cylindrical sleeve 16 for supporting the main crystal 30 therebetween.

Main crystal 30 can be an elongated multi-flat sided crystal with tapered multi-flat sided ends having pointed end tips, and can be chosen from materials such as a Lemurian Crystal, a quartz crystal, silicon dioxide, and the like. Main crystal 30 can be an elongated crystal with multi-faceted (up to approximately six sided flat faces) front tip end 32, cylindrical multi-faceted (up to approximately six sided flat faces) middle portion 34, 36 and multi-faceted (up to approximately six sided flat faces) rear tip end 38. Main crystal 30 can have dimensions of approximately 18 cm long by approximately 3 cm wide with ends 32, 38 tapering down to sharp tips with the ends 32, 38 having a length of approximately 2 cm.

Wrapped about a mid portion of main crystal 30 between front end 32 and rear end 36 can be an energy transfer coil 35 such as an electromagnet coil (such as but not limited to a copper wire coil).

Referring again to FIG. 1, and protruding from the rear middle portion 36 of main crystal 30 can be multi-faceted (up to approximately six sided flat faces) crystals 40, each protruding in a direction perpendicular to each of the flat faces on the sides of the rear tip end 38. Each of the side crystals 40 can be formed from materials such as a Lemurian Crystal, a quartz crystal, silicon dioxide, and the like. Side crystals 40 can each pass through side openings 19 in the housing sleeve 18 of the device 1. Side crystals 40 can have dimensions of approximately 2.5 cm long by approximately 1 cm wide. Side crystals 40 can be used as antennae to pickup ambient energy fields about the tool 1. Additionally, when used with the flash lamp 50/60, the side crystals will emit some flashing light, and their location can be used so that any operators of the tool position their hands to the right of the crystals 40 so that both the reflector 58 and shield 69 (both to be described later) help protect the operator from the tool 1.

Within rear housing sleeve 18 of tool 1 can be a U-shaped flash tube 50 with control board 60 such as but limited to a Velman Kit having a Strobro scope K5300 power plug and flash lamp. Additionally, a protective material 69 such as a foil shield, and the like, can be wrapped about these components to limit exposure to any operators. Behind flash tube 50 can be a curved reflector 58 having an interior concave mirrored face. Curved reflector 58 can be positioned about arms 52, 56 of flash tube 50, and curved portion 54 can abut against rear tip end 38 of main crystal 30.

The arms 52, 56 of flash tube 50 can be connected to a power supply 80/85 by electrical feed lines 62, 66 to the flash tube circuit control board 60. An on/off toggle type switch 72 can be connected by line 73 to the control board 60, to turn power on and off to the device 1. A variable control 76 such as a rotatable rheostat type control, connected by feed line 77 to control board 60, can control the flashing frequency of flash tube 50, which can flash across a frequency range of approximately 4 to approximately 15 Hertz.

Power to the tool 1 using the flash lamp 50/60 can be by an AC (alternating Current) 120 volt wall plug source 80.

Three different operational modes of using the tool 1 will now be described. A first operational mode uses just the flash lamp 50/60. A second mode uses only the electromagnetic coil 35 and exterior adapter 90. A third operational mode can combine the first and second modes.

In the operational mode using the flash lamp 50/60, the electromagnetic coil 35 and exterior adapter 90 are not used. Here the flash lamp 50/60 generates pulsing light to pass into the main crystal 30 which can be amplified by side antenna crystals 40, and further diffused and amplified by divergent lens 20 into the air and into a patient spaced away from the tool 1. The output beam 99 being generated can have a diameter of approximately 5 to approximately 6 cm and can be emitted in the range of approximately 4 to approximately 15 Hertz by varying the variable rheostat controller 76. The output beam 99 in tool 1 is substantially larger than that of the prior art Tens Cam described in the background section of the invention which was limited to a narrow beam of approximately 1 to approximately 2 millimeters.

In the second operational mode, a Tens Cam adapter such as that used in the prior art previously described can be used with tool 1, which can include an exterior pulse generator pack 90 can be used with tool 1. Exterior generator, can be connected by leads 89 that are attachable to a removable exterior connector plug 88 through interior leads 87 to electromagnetic coil 35 wrapped about main crystal 30. The exterior pulse generator 90 that can be used can be a Liss Body Stimulator Bipolar Model No. SBL-502-B. The generator 90 can include a battery power pack 92 having a 9 volt battery source, that powers a waveform signal generator component 94. The Tens Cam adapter embodiment contains an approximately 15,000 Hertz square wave carrier which can be rectified, varying from zero to a maximum of approximately 4 mill amperes. A first modulating signal of approximately 15 Hertz can provide an "on" time of approximately 50 milliseconds and an "off" time of approximately 16.7 milliseconds. A second modulating signal of approximately 500 Hertz changes the "on" time series of approximately 15,000 Hertz carrier pulses (approximately 750 pulses in approximately 50 milliseconds) into approximately 25 smaller bursts of approximately 15 pulses each of the 15,000 Hertz carrier signal (approximately 375 pulses in the same 50 milliseconds). The signals pass through the main crystal 30 by the electromagnetic coils 35 wrapped about crystal 30. With the adapter version 90 turned on by toggle type switch 92, a fixed emission of approximately 7.75 Hertz (approximately 8 Hertz) can be emitted from tool 1.

In the embodiment mode limited to using the electromagnetic adapter, square waves pass through electromagnetic coils 35 an into main crystal 30, the latter of which is amplified by side crystals 40. Signals passing from the tip end 32 of main crystal 30 are further amplified and diffused by lens 20 and pass into the air in a beam 99 having a diameter of approximately 5 to approximately 6 cm. As previously noted this diameter is substantially larger than the Tens Cam prior art device previously described in the background section of the invention. With the electromagnetic adapter 90, tool 1 can emit a fixed output emission of approximately 8 Hertz.

A third operational mode can combine both the first mode using the flash lamp 50/60 source and the second mode using the electromagnetic generator source 90.

Figure 2:
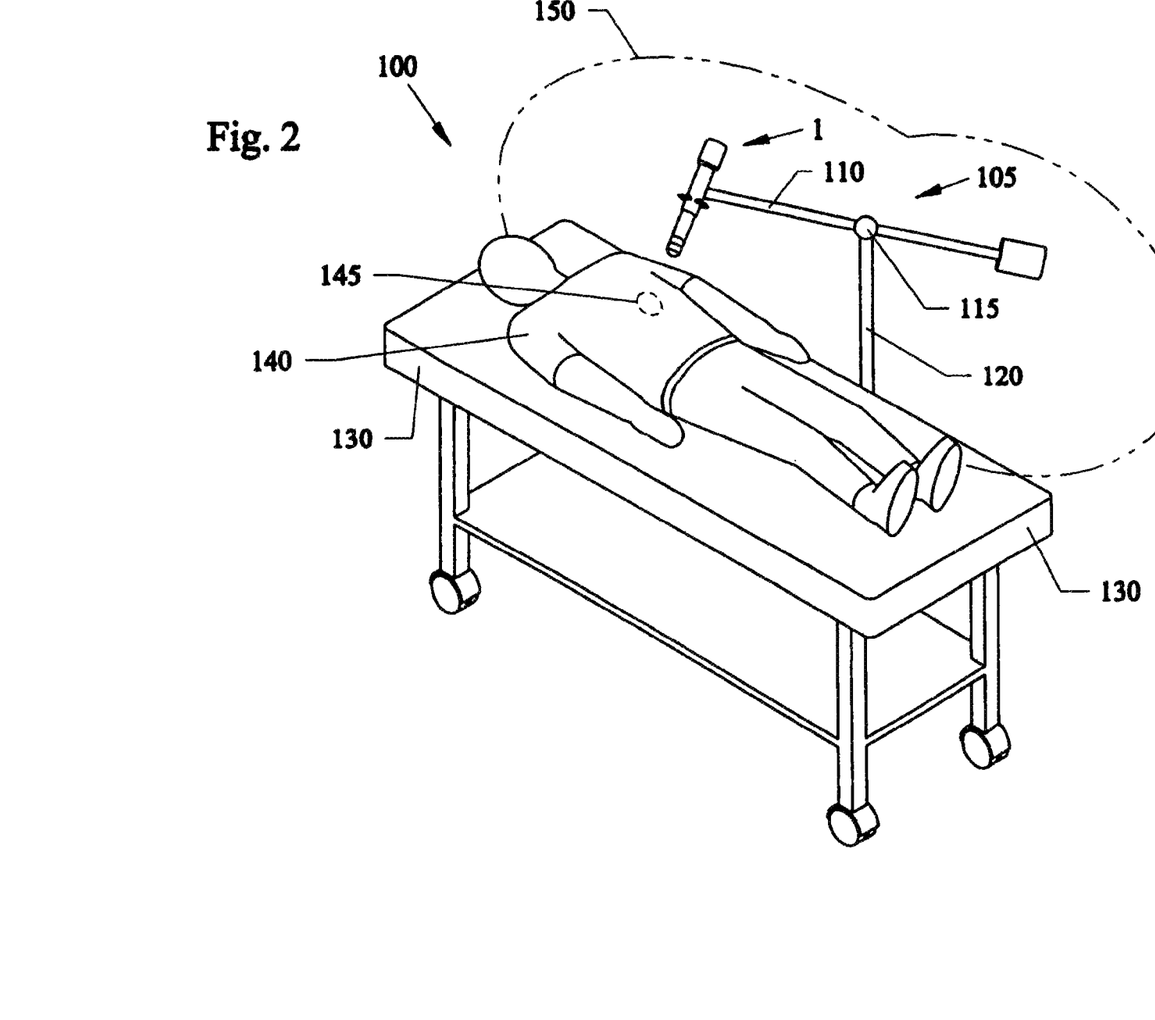
FIG. 2 shows the invention of FIG. 1 on a floor stand ready to be used before treatment.

FIG. 2 shows the invention device 1 of FIG. 1 on a floor stand 110/120 ready to be used before treatment. A floor stand 105 includes a floor supported vertical stand leg 120 with a boom arm 110 pivotally mounted on the stand leg 120, with the novel device 1 mounted to the boom arm 110. A patient 140 can be placed on a medical treatment table 130, such as being placed on their back. The flashing crystal 30 is visible through the clear window 14 (as shown in FIG. 1) in the device 1.

A health practitioner can position the arm 110 to a selected position over the patient 140 up to approximately 18 inches over the body part 145 being treated. The effected body part can be a gall bladder, joint pain, back pain, tissue damage, bone ligaments, organs, and the like. Additionally, t novel tool 1 can have therapeutic treatments for patients suffering from chronic type pain, joint pains, back pains, neck pains, hip pains, and shoulder pains.

Testing of the novel tool 1 using the three operational modes previously described has determined that treatment has been effective with various physically painful ailment areas such as those listed in Table 1 within time frames of up to approximately 2 minutes which is substantially less than the approximately 2 to approximately 4 minutes that was needed with the prior art Tens Cam unit. Ultrasounds taken from various patients have shown that less inflammation exists about the body areas these painful ailments occur. Thus, the tool 1 shows anti-inflammatory results in the areas listed in Table 1 below.

TABLE 1

| AILMENTS Column 1 List | AILMENTS Column 2 List |
| --- | --- |
| Ankle Sprain | Headache |
| Tennis Elbow | Earache |
| Torn Meniscus | Sinusitis |
| Back Pain | Burns |
| Nerve Root | Wounds |
| Bursitis | Abrasions |
| Neck Pain | GERD |
| Macular Degeneration | TMJ |
| Hernia | Morton's Neuroma |
| Gallbladder | Arthritis |
| Foot Pain | Sore Throat |
| Scars | Shingles |

Figure 3:
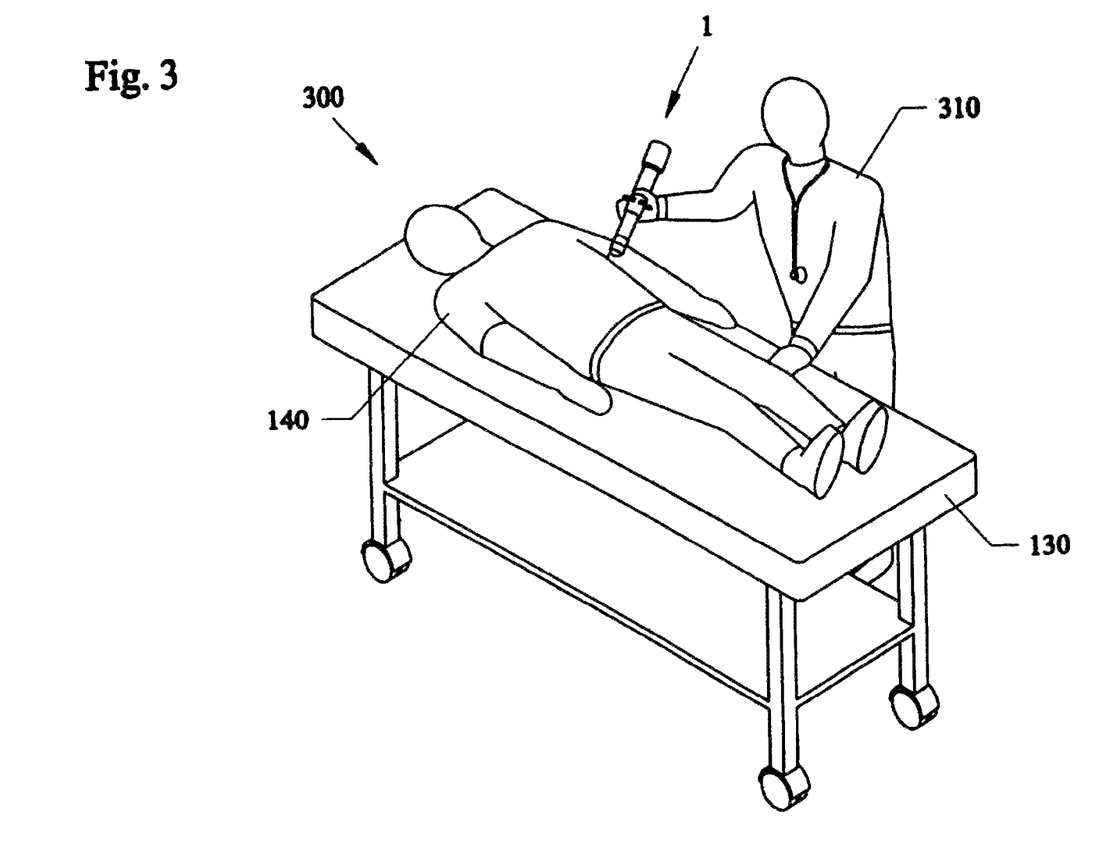
FIG. 3 shows the invention of FIG. 1 being handled by a healthcare practitioner.

FIG. 3 shows an application 300 the invention tool 1 of FIG. 1 being handled by a healthcare practitioner/operator 310. Operator 310 can physically hold tool 1 a selected position over the patient 140 up to approximately 18 inches over the body part 145 being treated, and has been similarly tested to show positive healing effects within approximately 2 minutes of being used which is substantially less than the approximately 2 to approximately 4 minutes that was needed with the prior art Tens Cam unit described in the background section of the invention. Referring to FIGS. 1 and 3, the protective shield 69 such as a foil wrap along with the reflector 58 having interior facing mirror surface that can be used inside of the tool helps eliminate any of fatigue and malaise results that have occurred to operators handling prior art tools.

Although one of the embodiments is described using a battery and another embodiment uses a wall plug power source, either or both embodiments can use battery and wall plug power supplies.

Additionally, although one embodiment has been described as using a fixed frequency output, and one embodiment using a variable emission output, either or both embodiments can generate fixed frequency outputs and/or variable frequency outputs.

Flashlight Handheld Version

Figure 4:
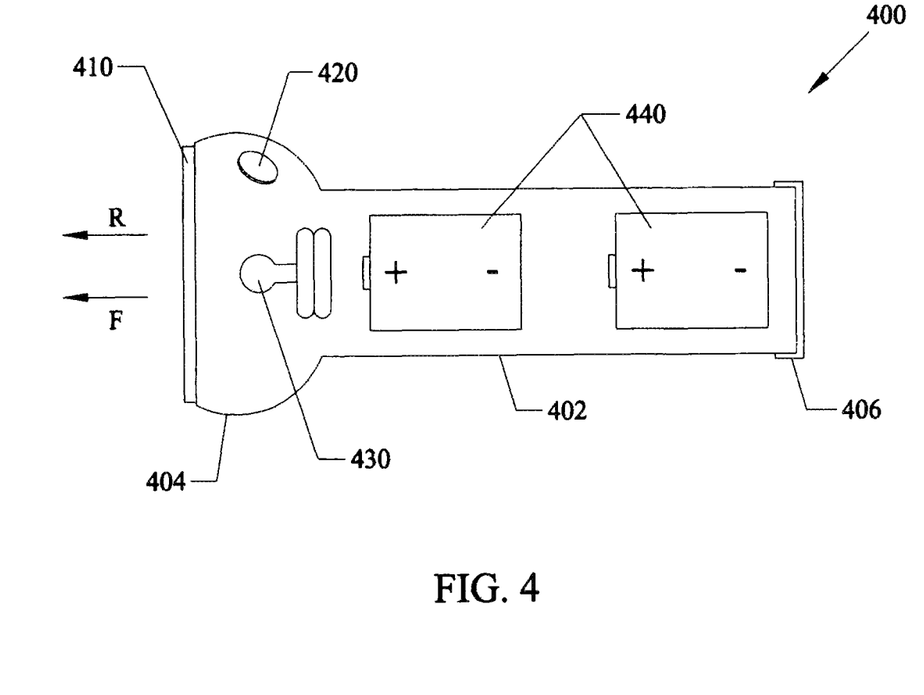
FIG. 4 is a cross-sectional view of a novel handheld flashlight version of the invention.

FIG. 4 is a cross-sectional view of a novel handheld flashlight version 400 of the invention. The handheld flashlight version of the invention relates to the embodiments described above and those described in U.S. patent application Ser. No. 10/084,008 filed Feb. 27, 2002, now allowed, entitled: Pulsecam by the same inventor and assignee as the subject invention, which is incorporated by reference.

FIG. 4 is a cross-sectional view of a novel handheld invention 400. The device 400 can include a lens emitting end cap 410 such as a flexible or rigid transparent plastic disc, and the like, that can have some focusing capability. The lens 410 can be located on one end of the housing covering the front face end of the head chamber portion 404. A bulb 430 can be mounted in the head chamber portion 404, and two batteries 440 such as but not limited to two nine volt batteries, two 3 volt batteries, and the like, can be mounted behind the bulb 430 in a cylindrical chamber 402, and a screwable end cap 406 can be used to cover the opposite end of the housing 400. The end cap 406 can be removable to allow the batteries 440 to be inserted and removed from the housing 400. Likewise the lens cap 410 may be removable by threads, and the like, to expose the inside of the head chamber portion 404.

A crystal 420, such as but not limited to a piezoelectric crystals, quartz crystals, and the like, having a diameter of approximately 6.35 millimeters (approximately ¼ inch square) or approximately 3 to approximately 4 millimeters (approximately 0.118 inches to approximately 0.157 inches) can be mounted in the head chamber 420 between the bulb 430 and lens cap 410. The crystal 420 can be positioned above or off-axis from the light beam F that can be emitted from the bulb.

The housing 400 can be similar to a flashlight body, such as but not limited to a mini magnum flashlight, and the like, where the user can easily grip about the cylindrical chamber housing portion 402 with one hand. The exterior housing surface of the cylindrical chamber 402 can be metal such as but not limited to aluminum, and the like, or nonconductive such as but not limited to plastic, and the like.

The exterior housing to the flashlight body can be used to conduct ambient energy from the person holding the device and/or ambient energy from the environment to the crystal. The crystal 420 can be powered from light energy from the bulb 430. Alternatively, the crystal 420 can be powered by electricity from the battery power supply 440. Still furthermore, the crystal can be electromagnetic energy, ambient energy, and/or any combination thereof.

The crystal 420 can generate a fixed output of approximately 7 to approximately 8 Hertz while the flashlight body is positioned up to approximately 18 inches over the body part being treated. Treatment effectiveness can occur within approximately 2 minutes of being treated.

The crystal 420 can be piezoelectric. The crystal can be formed from quartz, silicon dioxide, Lemurian Crystal, and the like. The battery power source 440 in the housing can have different size batteries where the housings have different sizes and shapes.

Alternatively, the invention can be powered by a wall plug, batteries, combinations thereof, and the like.

Still furthermore, the novel flashlight shaped version of the invention can be powered by a manual windup generator in an ergonomically shaped casing as shown in FIGS. 5-8.

The flashlight version of the invention incorporates the embodiments described above and which are also described in parent application U.S. patent application Ser. No. 10/084,008 filed Feb. 27, 2002, now allowed, entitled: Pulsecam by the same inventor and assignee as the subject invention, which is incorporated by reference.

For example, crystal 420 can also have other shapes, such as an elongated multi-flat sided crystal with tapered multi-flat sided ends having pointed end tips, and can be chosen from materials such as a Lemurian Crystal, a quartz crystal, silicon dioxide, and the like. Crystal 420 can be an elongated crystal with multi-faceted (up to approximately six sided flat faces) front tip end cylindrical multi-faceted (up to approximately six sided flat faces) middle portion and multi-faceted (up to approximately six sided flat faces) rear tip end.

Figure 5:
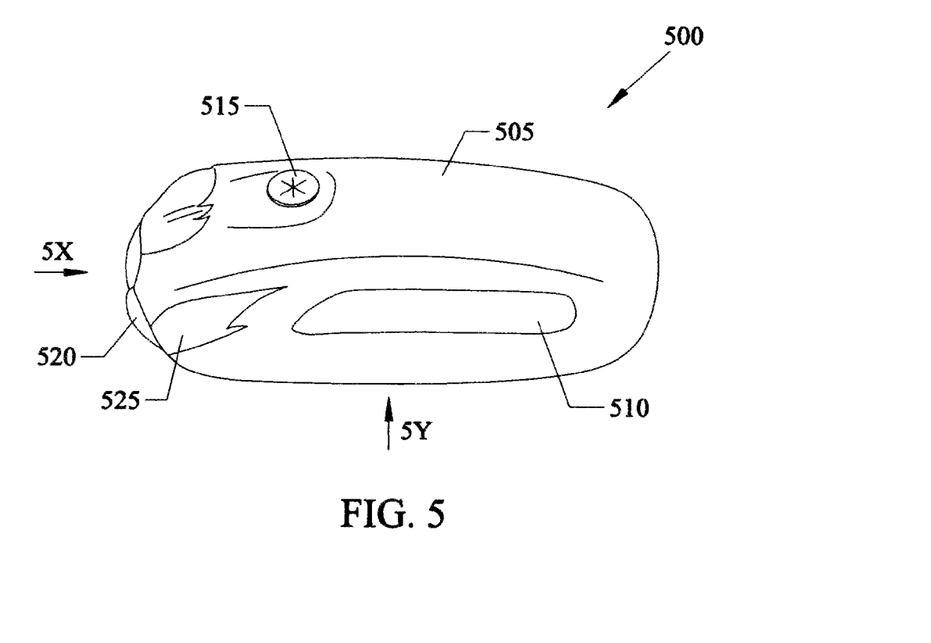
FIG. 5 is a side view of an ergonomic embodiment of the handheld flashlight version.
Figure 6:
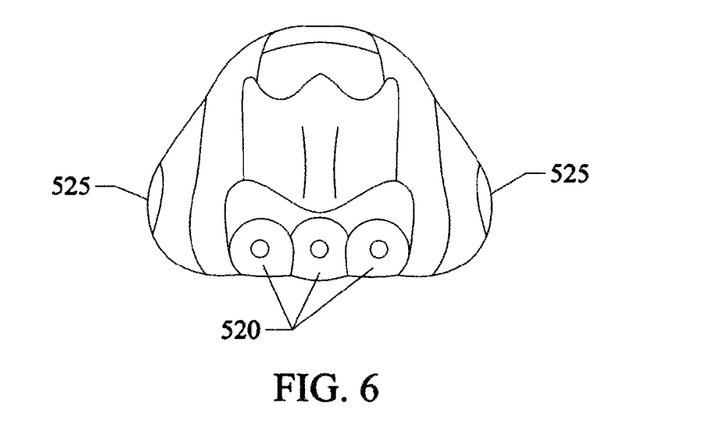
FIG. 6 is a front end view of the flashlight embodiment of FIG. 5 along arrow 5X.
Figure 7:
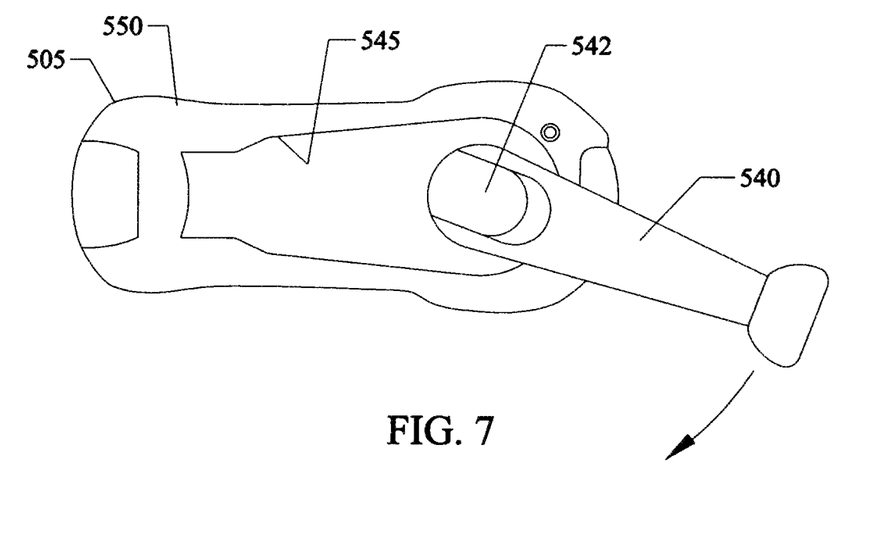
FIG. 7 is a bottom view of the flashlight embodiment of FIG. 5 along arrow 5Y.
Figure 8:
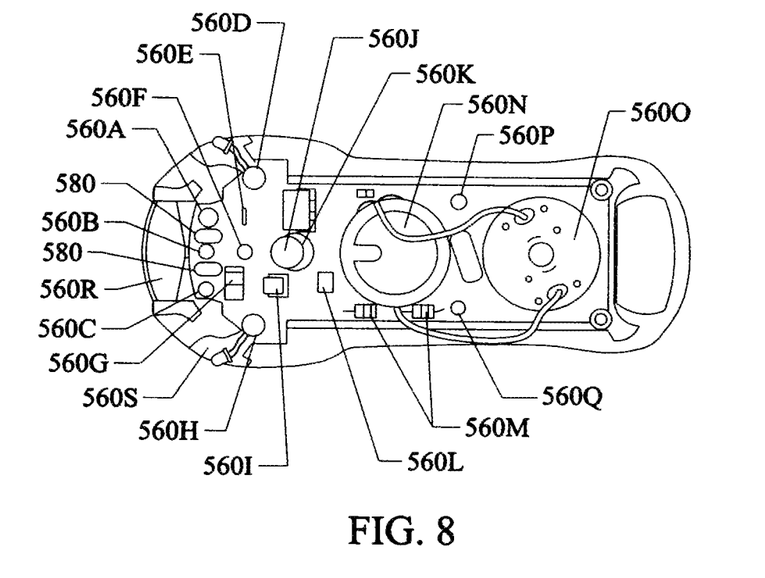
FIG. 8 is a cross-sectional view of the embodiment of FIG. 5.

FIG. 5 is a side view of an ergonomic embodiment 500 of the handheld flashlight version. FIG. 6 is a front end view of the flashlight embodiment 500 of FIG. 5 along arrow 5X. FIG. 7 is a bottom view of the flashlight embodiment 500 of FIG. 5 along arrow 5Y. FIG. 8 is a cross-sectional view of the embodiment 500 of FIG. 5.

Referring to FIGS. 5-8, the ergonomic embodiment 500 can have a plastic outer housing shell 505 having a length of approximately 5 to approximately 5½ inches, a width of approximately 1¾ inches to approximately 2½ inches, a weight of up to approximately 1¼ pounds, with rounded edges, and elongated gripping strips, such as but not limited to rubber, and the like, 510 along side walls for allowing the operator ease in gripping the unit shell 505. The top of the housing 505 can have a push button switch 515 which when depressed can activate power to the light sources 520, such as three LED (light emitting diodes). The unit can also include side frontal lights 525 that can also be colored LEDs or a white LED with a colored outer lens, such as yellow, and the like. The operator can use the main light sources 520 in order to aim the unit at the desired area to be treated on the patient.

The push button switch can have plural settings when depressed. For example, depressing the button 515 once turns on only the light sources 520 to emit a continuous light beam therefrom. Treatment from the unit can result in a continuous treatment signal from the crystal(s) inside of the unit. Optimal treatment has been tested during a flashing state. The close location of the crystals to the light sources allows for activation of treatment signals therefrom.

Depressing the button a second time can active both the light sources 520 and side emitting colored light sources 525 to a continuous on and off flashing state. The flashing state can result in a pulsed signal from the crystal(s) inside of the unit 505. If the side lights are not used, then the main light sources 520 can be used between two different settings that would indicate a continuous treatment signal or a pulsed treatment signal from the crystal(s) inside of the unit. Depressing the switch 515 a third time turns off power to the light sources.

Referring to FIGS. 7-8, the bottom of the unit housing 505 can include a handle 540, which can fold outward from a cavity 545 beneath the housing 505 by a rotatable hinge 542. In a folded out position, the operator can crank the handle by rotating in a clockwise direction (CW) which can charge the battery within the housing 505. Charging the battery to achieve a treatment time of approximately two minutes is generally needed. Two minute treatments can be done once a day for therapy. Testing has shown that at least approximately fifty complete (360 degree) rotations would achieve a two minute treatment time. After the battery is charged, the handle 540 can be folded back into the cavity 545.

The lower part of the housing 505 can include a removable bottom panel 550 that can be attached to the rest of the housing 505 by conventional fasteners, such as screws, and the like. Table 2 is a listing of the circuitry components that can be used.

TABLE 2

| | |
|---|---|
| 560A, 560B, 560C | Primary Blue/White LED (3 each) |
| 560D, 560H | Flashing Side LED (2 each) |
| 560E | Small signal diode |
| 560F, 560P, 560Q | Screw, circuit board retaining (3 each) |
| 560G | 50 Ohm Resistor (3 each) |
| 560I, 560L | Small signal transistor (2 each) |
| 560J, 560K | SPST Momentary Switch |
| 560M | Power Diodes (4 each) used to rectify the AC current coming from the generator. |
| 560N | Battery |
| 560O | Generator |
| 560R | Primary Lens |
| 560S | Side Lens (2 each) |
| 560T | Generator Drive Handle |
| 580 | Pair Of Crystals |

The crystals 580, can be piezo-electric, such as those previously described and can be at least two crystals each having diameters of approximately 2 mils to approximately 3 mils (less than approximately ¼ inch). Crystals can be fastened by glue, and the like, between each pair of LEDs 560A, 560B and 560C. The crystals 80 can be activated by induction from the LEDS 560A (520 in the previous figures). The embodiment 500 has been tested to achieve optimum therapeutic effects when the unit is in a flashing state. Thus, the switch being pushed twice, the output from the crystal 560A is at approximately 8 Hz which is a tested therapeutic modality level.

Referring again to FIGS. 4 and 5, in housings that replicate a large flashlight housing, crystal 420/580 can have dimensions of up to approximately 18 cm long by approximately 3 cm wide with ends, tapering down to sharp tips with the ends having a length of approximately 2 cm.

Optional extra crystals can be added that protrude from the rear middle portion of a main crystal can be multi-faceted (up to approximately six sided flat faces) crystals, each protruding in a direction perpendicular to each of the flat faces on the sides of the rear tip end. Optional side crystals can be formed from materials such as a Lemurian Crystal, a quartz crystal, silicon dioxide, and the like. Side crystals can each pass through side openings in the housing sleeve. Side crystals can have dimensions of approximately 2.5 cm long by approximately 1 cm wide. Side crystals can be used as antennae to pickup ambient energy fields about the tools 400/500.

Additionally, when used with the flash lamp, the side crystals will emit some flashing light, and their location can be used so that any operators of the tool position their hands to the right of the crystals so that both the reflector and a shield A health practitioner can position the flashlight housing 400/500 that houses the crystal 420/580 up to approximately 18 inches over the body part being treated. The effected body part can be a gall bladder, joint pain, back pain, tissue damage, bone ligaments, organs, and the like. Additionally, the novel tool 1 can have therapeutic treatments for patients suffering from chronic type pain, joint pains, back pains, neck pains, hip pains, and shoulder pains.

Thus, the flashlight tools 400/500 can be used to treat various anti-inflammatory results in the areas listed in Table 1 described above.

Additionally, the invention can generate a fixed frequency output, a variable emission output, and/or a combination thereof. Timers can be used to control outputs of the flashlight bulb.

Treatises have detailed how the solid state biochemistry and the piezoelectric characteristics of the cell wall relates to the electrical properties of the living cellular matrix. See for example, the book entitled: Energy Medicine, The Scientific Basis by Dr. James L. Oschman, Churchill Livingstone Publishers, 2000, on pages 51, 61 and 184. This book references the works of Dr. Robert Becker, MD, and his contribution of the perineural control system as it relates to limb growth and regeneration. Here the Schmann Resonance Theory is that the average alpha brain wave frequency in humans is 7.86 Hz, and that human tissue resonates at 7.86 Hz.

The subject inventor has incorporated these treatise teachings along with his tested inventions in Osteopathy Chiropractic treatments where the combination of structural and electromagnetic integration allows for the release of toxins and health improvements.

A prototype of the flashlight version of the invention was tested with the flashing (pulsed) version of the invention as depicted in FIGS. 5-8 above, over an approximately two minute period, by a Tektronics T922 portable oscilloscope with a calibration traceable to NIST. The oscilloscope measured output from the flashlight version prototype having a vibratory frequency output of approximately 8 Hz, while the light from the unit was flashing, a period per cycle of approximately 125 milliseconds, an amplitude of approximately 1.04 volts (approximately 5.1 divisions @ 200 millivolts/Div.).

In a preferred application of the handheld flashlight invention embodiment, treatment can be initiated by holding the tool 400/500 and optionally pointing by the emitted light beam aimed toward the painful problem area of the patient (such as those listed in Table 1 above). A painful problem can have an inflammation area, etc. The healing process can be started by having the patient exhaling through their nose and enhanced by having the mindset of the patient having the intention of the healing of the painful problem.

Tests have shown that the swelling will be seen to resolve first followed by nomalising of the normal tissue structure. Subjectively, pain has been shown to greatly become decreased. Objectively, testing has shown that an immediate decrease in swelling and redness will be noted. If an area of skeletal misalignment, was being treated the misalignment is usually corrected along with the pain, swelling and stiffness.

The portable flashlight version of the invention has been designed by the inventor to establish the normal body vibration pattern which allows the body to heal itself.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

I claim:

1. A method of treating patients with a handheld device, comprising the steps of:
   providing a portable lightweight flashlight;
   mounting a light source inside of the flashlight, the light source for emitting a light beam therefrom;
   mounting a crystal to be off-axis from the emitted light beam inside the flashlight;
   activating both the light source and the crystal; and
   generating a pulsed signal from the crystal wherein the pulsed signal is used for treatment of an effected area on a patient, and the device is adapted to be comfortably held in one hand of an operator without any fatigue to the operator.

2. The method of claim 1, wherein the generating step includes the step of:
   generating a vibratory output frequency of approximately 8 Hz.

3. The method of claim 1, wherein the crystal includes:
   at least two piezoelectric crystals.

4. The method of claim 1, wherein the crystal includes:
   a diameter of approximately 3 to approximately 4 millimeters.

5. The method claim 1, wherein the generating step includes the step of:
   generating a pulsed signal for approximately two minutes.

6. The method of claim 1, further comprising the step of:
   providing an ergonomic shaped elongated housing for the device having rounded and curved edges all around the device.

7. A method of providing medical treatments with a handheld device, comprising the steps of:
   providing a portable handheld flashlight housing having a head chamber and an elongated chamber behind the head chamber;
   covering an open end of the head chamber;
   positioning a light emitting source inside the head chamber behind the covering;
   positioning a piezoelectric crystal in the head chamber behind the covering with the crystal being adjacent, and not between the light source and the covering;
   providing power to the light emitting source from a power supply; and
   generating a resonating frequency between approximately 4 Hertz and 15 Hertz in the piezoelectric crystal that is adaptable as a treatment for an effected body part, wherein the housing being portable, lightweight and can be carried in one hand of an operator.

8. The method of claim 7, further comprising the steps of:
   focusing the crystal generated resonating frequency toward an effected body part for treatment for up to approximately 2 (two) minutes.

9. The method of claim 7, further comprising the steps of:
   providing a handheld grip exterior surface about the housing; and
   positioning the device up to approximately 18 inches above the effected body part being treated by gripping the grip exterior surface about the housing.

10. The method of claim 7, wherein the generating step includes the step of: generating a fixed resonating frequency between approximately 7 to approximately 8 Hertz.

11. The method of claim 7, wherein the generating step includes the step of: generating a variable range resonating frequency between approximately 4 to approximately 15 Hertz.

12. The method of claim 7, wherein the covering step includes the step of:
   diffusing and amplifying signals from the piezoelectric crystal with a lens.

13. The method of claim 7, wherein the step of positioning includes the step of:
   positioning the crystal to be off-axis to the light beam that is emitted from the light emitting source.

14. A method of providing medical treatments with a handheld device, comprising the steps of:
   providing a portable handheld flashlight housing having a head chamber and an elongated chamber behind the head chamber;
   covering an open end of the head chamber;
   positioning at least one light emitting diode (LEDs) inside the head chamber behind the covering;
   positioning at least one crystal in the head chamber next to the light emitting diode (LED);
   providing power to the light emitting diode from a power supply; and
   generating a resonating frequency from the at least one crystal the resonating frequency being selected from one of a fixed frequency of approximately 7 to approximately 8 Hertz, and a variable range of approximately 4 Hertz to approximately 15 Hertz; and
   treating an affected body part with the resonating frequency.

15. The method of claim 14, wherein the step of positioning at least one light emitting diode (LED) includes the step of:
   positioning a plurality of light emitting diodes (LEDs).

16. The method of claim 15, wherein the step of positioning at least one crystal includes the step of:
   positioning a plurality of crystals, each crystal being located next to each light emitting diode (LED).

17. The method of claim 14, wherein the step of positioning at least one crystal includes the step of:
   positioning the at least one crystal to be off-axis to the light beam that is emitted from the at least one light emitting diode (LED).

18. The method of claim 14, wherein the at least one crystal is a piezoelectric crystal.

* * * * *